United States Patent [19]

Zurmühlen

[11] Patent Number: 5,523,404

[45] Date of Patent: Jun. 4, 1996

[54] PROCESS FOR PREPARING 5-CHLORO-4-HYDROXYPYRIMIDINES

[75] Inventor: Frank Zurmühlen, Frankfurt am Main, Germany

[73] Assignee: Hoechst Schering AgrEvo GmbH, Berlin, Germany

[21] Appl. No.: 271,177

[22] Filed: Jul. 7, 1994

[30] Foreign Application Priority Data

Jul. 10, 1993 [DE] Germany .................. 43 23 180.2

[51] Int. Cl.[6] ...................... C07D 239/30; C07D 239/34
[52] U.S. Cl. ............................. 544/319; 544/334
[58] Field of Search ..................... 544/319, 334

[56] References Cited

U.S. PATENT DOCUMENTS 4,199,600  4/1980  Brandman et al. ............. 424/314

FOREIGN PATENT DOCUMENTS 0326389  1/1989  European Pat. Off. .
0370391  11/1989  European Pat. Off. .
0568041  4/1993  European Pat. Off. .

OTHER PUBLICATIONS

*Chemical Abstracts*, 109(9): 73464h, Wenger et al (1988).
*Beilstein*, 1811955 Abstract of Genvresse, Ann. Chim. (Paris) vol. 24, p. 64 (1891).
*Chemical Abstracts*, 93(7): 63604r Brandman et al (1980).
*Chemical Abstracts*, 82(5): 31347r, Bertin et al (1974).

*Primary Examiner*—John M. Ford
*Attorney, Agent, or Firm*—Curtis, Morris & Safford

[57] ABSTRACT

A process for preparing 5-chloro-4-hydroxypyrimidines, 2-chloro enamines as intermediates in this process and their use The invention relates to a process for preparing compounds of the formula

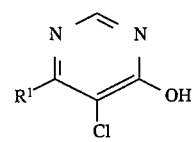

in which $R^1$ is optionally substituted alkyl, cycloalkyl, aryl or benzyl, in which a chloroacetic ester is converted with ammonia or an ammonium salt into the corresponding chloro enamine and the latter is condensed in the presence of a base with formamide. The invention furthermore relates to 2-chloro enamines as intermediates in the process.

11 Claims, No Drawings

PROCESS FOR PREPARING 5-CHLORO-4-HYDROXYPYRIMIDINES

5-Chloro-4-hydroxypyrimidines are important intermediates for preparing crop protection agents and pharmaceuticals as proposed, for example, in PCT/EP 93/00536.

5-Chloro-4-hydroxypyrimidines are also called 5-chloro-4-pyrimidones or 5-chloro-4-pyrimidinols. They are generally prepared by chlorination of 4-hydroxypyrimidines in position 5. Chlorinating agents used for this purpose are, for example, N-chlorosuccinimide, sodium hypochlorite, thionyl chloride [D. J. Brown, The Chemistry of Heterocyclic Compounds, The Pyrimidines (1962); ibid.; The Pyrimidines Supplement I (1970); ibid., The Pyridimines Supplement II (1985); all published by John Wiley & Sons Inc., New York] or chlorine gas [JP 8222070]. In these cases the yields are frequently poor, which is unfavorable for an industrial process. It is also a disadvantage that the 4-hydroxypyrimidines required as starting materials can be obtained only with difficulty.

The previously disclosed processes leading to 4-hydroxy-pyrimidines are to be dealt with in detail hereinafter.

In the first case, a β-keto acid ester is condensed with thiourea to give the corresponding 2-thiouracil, and subsequently sulfur is removed with Raney nickel [H. M. Foster, H. R. Snyder, Org. Synth., Coll. Vol. IV, 638]. However, this sulfur removal is impractical for an industrial process.

Another process described for preparing 4-hydroxypyrimidines is the condensation reaction of a β-keto acid ester with formamidine acetate [M. Butters, J. Heterocycl. Chem., 29, 1369 (1992)]. However, the yield of this reaction is very low, and the amount of salt produced is relatively high; in addition, formamidine acetate is a relatively costly condensing agent so that this process does not represent an industrial alternative.

Another possible preparation of 4-hydroxypyrimidines is the reaction of an enamine prepared from a β-keto ester with formamide [EP-A-0326389]. This synthesis is suitable per se for an industrial process but has the disadvantage that 4-hydroxypyrimidines unsubstituted in position 5, in particular with short-chain alkyl radicals, are considerably more difficult to work up, because of their high solubility in water, than the corresponding representatives substituted with chlorine in position 5. Because of these losses on workup, and owing to the previously mentioned losses in the subsequent 5-chlorination, this is a disadvantageous route for the purposes of an industrial synthesis.

By contrast, it is significantly more favorable to carry out a condensation reaction in which there is direct formation of a 5-chloro-4-hydroxypyrimidine.

A process of this type, in which 2-chloro-β-keto acid esters are reacted with formamidine salts to give 5-chloro-4-hydroxypyrimidines directly has already been described [EP-A-0370391]. However, this process has the disadvantage that it depends on the use of a relatively costly condensing agent in formamidine acetate. In addition, the waste situation is not without problems; the unfavorable stoichiometry unavoidably leads to polymerization of the part of the formamidine acetate which is used in excess, and it cannot therefore be recovered. Furthermore, a large base excess is necessary to liberate formamidine from its salt, which is associated with a heavy salt load.

The object of the invention was therefore to find a process for preparing 5-chloro-4-hydroxypyrimidines which can be carried out on an industrial scale using a low-cost condensing agent and displays a favorable environmental balance (=small amount of salt produced).

The object according to the invention is surprisingly achieved by converting a 2-chloro-β-keto ester with ammonia or an ammonium salt into the corresponding enamine, which is subsequently condensed with formamide to give 5-chloro-4-hydroxypyrimidine. Of the enamines used as intermediates for this, ethyl 3-amino-2-chlorocrotonate has already been disclosed in Ann. Chim. (Paris) 24 [1891] p. 64.

The invention therefore relates to a process for preparing 5-chloro-4-hydroxypyrimidines of the formula I

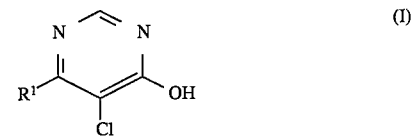

which comprises reacting a 2-chloro-β-keto ester of the formula II

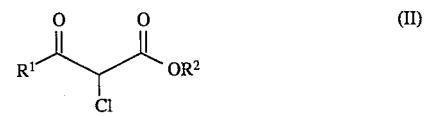

with ammonia or the ammonium salt of, preferably, an organic acid to give a 2-chloro enamine of the formula III

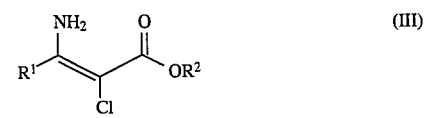

(the reaction can be carried out in polar protic or aprotic solvents or without solvents), which is subsequently condensed in a polar protic solvent in the presence of a base with formamide to give the compound of the formula I.

The process according to the invention is preferably carried out without isolation of the 2-chloro enamine of the formula III (as "one-pot reaction").

There is then, for example, the possibility of reacting the resulting product of the formula I with POCl₃ in a manner known per se to give a 4,5-dichloropyrimidine of the formula IV

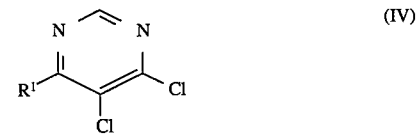

In the formulae I–IV,

R¹ is optionally substituted alkyl, cycloalkyl, aryl or benzyl,

R² is alkyl, benzyl or another carboxyl protective group.

R¹ is preferably $(C_1-C_4)$-alkyl, $(C_1-C_4)$-haloalkyl, $(C_1-C_4)$-alkoxy-$(C_1-C_4)$-alkyl or $(C_1-C_4)$-alkylthio-$(C_1-C_4)$-alkyl, in particular $(C_1-C_4)$-alkyl, such as methyl or ethyl, or methoxymethyl; ethyl is very particularly preferred.

R² is preferably $(C_1-C_4)$-alkyl, benzyl or another carboxyl protective group, in particular $(C_1-C_4)$-alkyl, such as methyl, ethyl or tert-butyl, benzyl or modified benzyl; methyl is very particularly preferred.

Unless otherwise defined in the specific case, alkyl is straight-chain or branched and is preferably $(C_1-C_6)$-alkyl, such as methyl, ethyl, propyl, isopropyl, butyl, tert-butyl, pentyl or hexyl. A corresponding statement applies to radicals derived therefrom, such as alkoxy, alkylthio and haloalkyl.

Cycloalkyl preferably has 3 to 8 carbon atoms and represents radicals such as cyclobutyl, cyclopentyl and cyclohexyl.

Aryl preferably has 6 to 12 carbon atoms and is, for example, phenyl, naphthyl or biphenylyl; phenyl is preferred.

Substituted alkyl, cycloalkyl, aryl or benzyl is preferably substituted by 1 to 3 identical or different radicals which are inert under the conditions of the process according to the invention and are selected from halogen, $(C_1-C_4)$-alkoxy, $(C_1-C_4)$-alkylthio and, in the case of the cyclic radicals, $(C_1-C_4)$-alkyl.

Halogen means fluorine, chlorine, bromine or iodine, preferably fluorine or chlorine.

Haloalkyl is an alkyl radical which is as defined above and in which one, a plurality of or all the hydrogen atoms are replaced by identical or different halogen atoms.

Carboxyl protective groups are described, for example, in Hubbuch, Kontakte Merck 3/79, pages 14 and 19 ff. Frequently used are methyl, ethyl, benzyl and tert-butyl, as well as modified benzyl radicals such as p-chlorobenzyl, p-nitrobenzyl and p-methoxybenzyl.

The invention also relates to 2-chloro enamines of the formula II in which $R^1$ and $R^2$ are as defined above, excepting ethyl 3-amino-2-chlorocrotonate.

The 2-chloro-β-keto esters depicted in formula I can be prepared in a known manner by chlorination of the corresponding β-keto esters with sulfuryl chloride either using an aprotic solvent or without solvents [W. R. Böhme, Org. Synth. Coll. Vol. IV, 590 (1963)] and with chlorine gas as chlorinating agent.

The 2-chloro enamine of the formula II can be prepared by using the crude product from stage 1 after removal of the solvent and the gases. The reaction can be carried out with $NH_3$ gas without solvent, in polar protic solvents such as alcohols or formamide or in polar aprotic solvents, for example dioxane, dimethylformamide or acetonitrile. It is also possible to use ammonium salts as ammonia donors in place of $NH_3$. Alcohols used are lower alcohols such as methanol, ethanol, isopropanol or butanol. When ammonium salts are used, addition of polyethylene glycol effects an increase in the yield.

The reaction can be carried out in a temperature range from −40° to 80° C. preferably from 20° to 78° C. Ammonium salts which are preferably used are ammonium salts of the carboxylic acids such as formic acid, acetic acid, oxalic acid or of carbonic acid. Working up is preferably carried out under anhydrous conditions by removing the solvent in vacuo and then dissolving the substance in an aprotic solvent such as diisopropyl ether or methyl isobutyl ketone, and removing excess ammonium salt by filtration. The recovered ammonium salt can be reused.

Polar protic solvents such as water, methanol, ethanol, i-propanol or butanol are preferably used for the condensation reaction. It is preferable to use the alcohol which corresponds to the relevant ester, i.e. methanol or ethanol. In an azeotropic procedure it is advantageous to add the required amount of an entrainer, for example toluene.

Alkali metal alcoholates, hydroxides, carbons or bicarbonates are used as bases. The preferred procedure uses an alkali metal alcoholate in the corresponding alcohol. In this case it is possible where appropriate to add a desiccant, for example magnesium sulfate or 30 nm molecular sieves, to bind the water being liberated in the reaction. The reaction temperature is between 20° and 80° C. It is preferable to use an excess of 1.5–3.5 mol of the theoretically required formamide. Part of the excess formamide is not used during the reaction and can be reused after distillation. 1–2.2 mol of base are needed for 1 mol of 2-chloro enamine of the formula II used. After the reaction is complete, the prepared 5-chloro- 4-hydroxypyrimidine of the formula III can, after dissolving in water, be extracted by extraction with a polar solvent at a pH of 3–7. With some derivatives, the 5-chloro-4-hydroxypyrimidine crystallizes out of water at the stated pH so that it can subsequently be filtered off with suction.

However, it is also possible to react the crude product, after acidification to pH 3–7 and removal of the solvent in vacuo, without further purification with $POCl_3$ to give the corresponding 4,5-dichloropyrimidine.

The following examples illustrate the invention without intending to restrict it to them.

Example 1

Methyl 3-amino-2-chloro-2-pentenoate

Dry $NH_3$ gas is passed through 48.9 g (0.30 mol) of methyl 2-chloro-3-oxovalerate at 70° C. for a period of 2 h. After removal of volatile constituents in vacuo, the crude product is dissolved in diisopropyl ether and washed with a little ice water. After drying over $MgSO_4$, the solvent is removed in vacuo. Yield: 80.0% [GC]

Example 2

Methyl 3-amino-2-chloro-2-pentenoate

A solution of 576.1 g (3.5 mol) of methyl 2-chloro-3-oxovalerate and 674.5 g (8.75 mol) of ammonium acetate in 1.2 l of methanol is heated at 65° C. with stirring for a period of 4 h. After cooling, the solvent is removed in vacuo, the residue is taken up in 2.5 l of diisopropyl ether, and the solid is removed. The solid is dissolved in a little water and subsequently extracted with ethyl acetate. The organic fractions are combined, dried over $MgSO_4$ and evaporated in vacuo. Yield: 94.7% [GC]

Example 3

Methyl 3-amino-2-chloro-2-pentenoate

A solution of 47.5 g (0.75 mol) of ammonium formate and 49.0 g (0.3 mol) of methyl 2-chloro-3-oxovalerate in 800 ml of ethanol is reacted and worked up in analogy to Example 2. Yield: 72.0% [GC]

Example 4

Methyl 3-amino-2-chloro-2-pentenoate

Dry $NH_3$ gas is passed through a solution of 376.3 g (2.064 mol) of methyl 2-chloro-3-oxovalerate in 100 ml of methanol while stirring at 65° C. for 3 h. The solvent is removed in vacuo, the residue is taken up in diisopropyl ether, the solution is filtered through sea sand, and the solvent is evaporated. Yield: 87.6% [GC]

Example 5

Methyl 3-amino-2-chloro-2-butenoate 50 g (0.33 mol) of methyl 2-chloroacetoacetate are reacted with 64 g (0.83 mol) of ammonium acetate in 100 ml of methanol and worked up in analogy to Example 2. Yield: 63.9% [GC]

Example 6

Ethyl 3-amino-2-chloro-2-hexenoate 61.5 g (0.32 mol) of ethyl 2-chloro-3-oxohexanoate are reacted with 61.5 g (0.80 mol) of ammonium acetate in 120 ml of methanol and worked up in analogy to Example 2. Yield: 95.5% [GC]

Example 7

Ethyl 3-amino-2-chloro-4-methyl-2-pentenoate 59.5 g (0.31 mol) of ethyl 2-chloro-4-methyl-3-oxo-pentanoate are reacted with 59.8 g (0.78 mol) of ammonium acetate in 120 ml of methanol and worked up in analogy to Example 2. Yield: 88.0% [GC]

Example 8

Ethyl 3-amino-2-chloro-3-phenylpropenoate 58.25 g (0.26 mol) of ethyl 2-chlorobenzoylacetate are reacted with 49.52 g (0.64 mol) of ammonium acetate in 100 ml of methanol and worked up in analogy to Example 2. Yield: 91.6% [GC]

Example 9

5-Chloro-6-ethyl-4-hydroxypyrimidine

A mixture of 163.6 g (1.0 mol) of methyl 3-amino-2-chloro-2-pentenoate, 90.8 g (2.0 mol) of formamide and 150 ml of methanol is added dropwise with stirring to 485.8 ml of a 30% strength NaOMe solution in methanol at room temperature. The mixture is subsequently slowly heated to the reflux temperature over the course of 3 h, and is left to stir at this temperature for a further 12 h. Evaporation of the reaction mixture is followed by dissolving in a little $H_2O$, adjustment to a pH of 3.8 with HCl and extraction with ethyl acetate. Drying over $MgSO_4$ and evaporation provide 177.5 g of crude product which is subsequently recrystallized from water. Yield: 130.4 g (82%)

Example 10

5-Chloro-6-ethyl-4-hydroxypyrimidine

Two dropping funnels are used for simultaneous dropwise addition of a solution of 35.5 g (0.2 mol) of methyl 3-amino-2-chloro-2-pentenoate and 31.5 g (0.7 mol) of formamide in 150 ml of methanol with stirring to 90.3 ml of a 30% strength sodium methylate solution in methanol at room temperature. The mixture is heated slowly to the reflux temperature and left at this for 10 h. After the mixture has cooled, dry HCl gas is passed through the solution until the pH is 3. Evaporation of the solvent is followed by extraction with butanone, drying and evaporation in a rotary evaporator. Yield: 87% [HPLC]

Example 11

5-Chloro-4-hydroxy-6-methylpyrimidine 25.9 g (0.17 mol) of methyl 3-amino-2-chloro-2-butenoate are reacted with 11.7 g (0.26 mol) of formamide and 51 ml of sodium methylate solution in 20 ml of methanol and worked up in analogy to Example 9 (reaction time 20 h). Yield: 16.6 g (67.5%)

Example 12

5-Chloro-4-hydroxy-6-propylpyrimidine 58.1 g (0.30 mol) of ethyl 3-amino-2-chloro-2-hexenoate are reacted with 47.7 g (1.1 mol) of formamide and 140 ml of sodium methylate solution in 175 ml of methanol and worked up in analogy to Example 9 (reaction time 6 h). Yield: 42.2 g (81.5%)

Example 13

5-Chloro-4-hydroxy-6-phenylpyrimidine 45.73 g (0.20 mol) of ethyl 3-amino-2-chloro-3-phenylpropenoate are reacted with 31.9 g (0.71 mol) of formamide and 93 ml of sodium methylate solution in 120 ml of methanol and worked up in analogy to Example 9 (reaction time 16 h). Yield: 32.9 g (79.7%)

Example 14

5-Chloro-4-hydroxy-6-isopropylpyrimidine 45.1 g (0.24 mol) of ethyl 3-amino-2-chloro-4-methyl-2-pentenoate are reacted with 36.8 g (0.59 mol) of formamide and 109 ml of sodium methylate solution in 130 ml of methanol and worked up in analogy to Example 9. Yield: 34.5 g (83.3%)

Example 15

4,5-Dichloro-6-ethylpyrimidine (one-pot process)

134.0 g (0.82 mol) of methyl 3-amino-2-chloro-2-pentenoate and 125.3 g of formamide, dissolved in 150 ml of methanol, are simultaneously added dropwise with stirring to 357.8 ml of a 30% strength sodium methylate solution in methanol at room temperature. The mixture is heated to the reflux temperature over the course of 5 h and is then left at this for 10 h. After cooling, dry HCl gas is passed through until the pH reaches 3. The solvent and the excess formamide are removed by distillation and subsequently 100 ml of toluene are added and removed by distillation twice. 145.3 ml of $POCl_3$ are added to the mixture, which is heated at 70°–80° C. with stirring for 5 h. The excess $POCl_3$ is then removed by distillation, the mixture is added to ice water and neutralized with $K_2CO_3$. The residue after extraction with ethyl acetate and evaporation of the solvent is distilled at 110°–112° C. under 25 mbar. Yield: 114.0 g (78.5%)

Example 16

5-Chloro-6-ethyl-4-hydroxypyrimidine $NH_3$ gas is passed with cooling (max. 50° C.) through a solution of 99.7 g (0.6 mol) of methyl 2-chloro-3-oxovalerate in 130 ml of formamide until the mixture takes up no more $NH_3$ (about 1 h). The ammonia residues are removed by blowing out with nitrogen and applying a vacuum. The reaction solution is subsequently added dropwise to 450 ml of a 30% NaOMe solution in methanol at 50° C. Addition of a further 50 ml of formamide is followed by heating at 50° C. for 3 h. The volatile constituents are evaporated in vacuo, and subsequently the mixture is added to water and the pH is adjusted to 6 with HCl. Extraction with ethyl acetate and evaporation provide 91.2 g of crude product, which is recrystallized from cold acetone. Yield: 66.3 g (70%)

Example 17

5-Chloro-6-ethyl-4-hydroxypyrimidine

Dry $NH_3$ gas is passed with cooling (reaction temperature max. 50° C.) through a solution of 150 g (0.88 mol) of methyl 2-chloro-3-oxovalerate in 100 ml of methanol until the mixture takes up no more $NH_3$ (2.5 h). The ammonia residues are removed by blowing out with $N_2$ and briefly applying a vacuum. Subsequently, 140 ml of formamide are added, and the solution is added dropwise to 472 ml of a 30% NaOMe solution in methanol at 50° C. Heating at 50° C. for 4 h is followed by working up in analogy to Example 16. Yield: 114.4 g (82%)

I claim:

1. A process for preparing a compound of the formula I

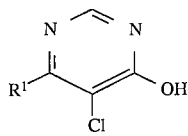

(I)

in which $R^1$ is $(C_1-C_4)$-alkyl, $(C_1-C_4)$-haloalkyl, $(C_3-C_8)$-cycloalkyl, phenyl, naphthyl, biphenyl or benzyl, or such alkyl, cycloalkyl, phenyl, naphthyl, biphenyl or benzyl substituted with 1, 2 or 3 identical or different radicals selected from the group consisting of halogen, $(C_1-C_4)$-alkoxy, $(C_1-C_4)$-alkylthio and, in the case of the last five named radicals, $(C_1-C_4)$-alkyl, which process comprises reacting a compound of the formula II

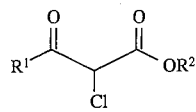

(II)

n which $R^1$ is as defined above, and $R^2$ is $(C_1-C_4)$-alkyl, benzyl or modified benzyl, with ammonia or an ammonium salt to give a compound of the formula III

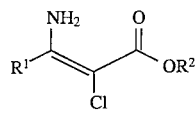

(III)

in which $R^1$ and $R^2$ are as defined above, which is subsequently condensed in a polar protic solvent in the presence of a base with formamide to give a compound of the formula I.

2. A process as claimed in claim 1 wherein the intermediate of the formula III is not isolated.

3. A process as claimed in claim 1, wherein compounds of the formula I in which $R^1$ is $(C_1-C_4)$-alkyl, $(C_1-C_4)$-haloalkyl, $(C_1-C_4)$-alkoxy-$(C_1-C_4)$-alkyl or $(C_1-C_4)$-alkylthio-$(C_1-C_4)$-alkyl are prepared.

4. A process as claimed in claim 1, wherein compounds of the formula I in which $R^1$ is $(C_1-C_4)$-alkyl are prepared.

5. A process as claimed in claim 1, wherein compounds of the formula I in which $R^1$ is selected from the group consisting of methyl, ethyl, or methoxymethyl, are prepared.

6. A process as claimed in claim 1, wherein compounds of the formula I in which $R^1$ is ethyl are prepared.

7. A process as claimed in claim 1, which starts from compounds of the formula II in which $R^2$ is $(C_1-C_4)$-alkyl or benzyl.

8. A process as claimed in claim 1, which starts from compounds of the formula II in which $R^2$ is $(C_1-C_4)$-alkyl.

9. A process as claimed in claim 1, which starts from compounds of the formula II in which $R^2$ is selected from the group consisting of methyl, ethyl, tert-butyl, benzyl or modified benzyl.

10. A process as claimed in claim 1, which starts from compounds of the formula II in which $R^2$ is methyl.

11. A compound of the formula III as claimed in claim 1, in which $R^1$ and $R^2$ are as defined in claim 11, excepting 3-amino-2-chloro-but- 2-enoic acid $(C_1-C_4)$-alkylesters.

* * * * *